(12) United States Patent
Myron et al.

(10) Patent No.: US 12,402,845 B2
(45) Date of Patent: Sep. 2, 2025

(54) BIOMETRIC SENSORS FOR ENHANCED DETECTION, STIMULATION, AND NOTIFICATION

(71) Applicant: T-MOBILE INNOVATIONS LLC, Overland Park, KS (US)

(72) Inventors: Peter Philip Myron, New Braunfels, TX (US); Michael John Mitchell, North Bend, WA (US)

(73) Assignee: T-Mobile Innovations LLC, Overland Park, KS (US)

( * ) Notice: Subject to any disclaimer, the term of this patent is extended or adjusted under 35 U.S.C. 154(b) by 245 days.

(21) Appl. No.: 18/184,069

(22) Filed: Mar. 15, 2023

(65) Prior Publication Data

US 2024/0307006 A1 Sep. 19, 2024

(51) Int. Cl.
*A61B 5/00* (2006.01)
*A41D 13/12* (2006.01)
*A61B 5/145* (2006.01)

(52) U.S. Cl.
CPC .......... *A61B 5/746* (2013.01); *A41D 13/1281* (2013.01); *A61B 5/14532* (2013.01); *A61B 5/4266* (2013.01); *A61B 5/7455* (2013.01)

(58) Field of Classification Search
CPC ... A61B 5/746; A61B 5/14532; A61B 5/4266; A61B 5/7455; A61B 5/6804; A41D 13/1281; A41D 1/002
See application file for complete search history.

(56) References Cited

U.S. PATENT DOCUMENTS

| | | | |
|---|---|---|---|
| 2015/0370320 A1* | 12/2015 | Connor | A61B 5/1121 345/173 |
| 2017/0010672 A1* | 1/2017 | Tanaka | G06F 1/3206 |
| 2020/0138377 A1* | 5/2020 | Huijbregts | A61B 5/681 |
| 2022/0132946 A1 | 5/2022 | Walker | |
| 2022/0181015 A1* | 6/2022 | Mattoon | G16H 40/67 |

* cited by examiner

*Primary Examiner* — Omeed Alizada
(74) *Attorney, Agent, or Firm* — Shook Hardy & Bacon L.L.P.

(57) ABSTRACT

The technologies discussed herein relate to a biometrics system comprising one or more processors, computer storage memory having computer-executable instructions, surgically implantable devices, and wearables (e.g., an apparel item configured for an upper torso, an apparel item configured for a lower torso, a sock, a headband, other types of wearables, or one or more combinations thereof) having one or more biometric sensors (e.g., a heart rate sensor, a sweat sensor, a glucose sensor, other types of biometric sensors, or one or more combinations thereof) and one or more sensation devices (e.g., a plurality of visible light sources, a haptic feedback device, other types of sensation devices, or one or more combinations thereof). The wearables may also include one or more environmental sensors. The wearables emulate, transmogrify, or enhance one or more human senses using the one or more sensation devices based on biometric data or environmental data received.

20 Claims, 6 Drawing Sheets

BIOMETRIC SENSORS FOR ENHANCED DETECTION, STIMULATION, AND NOTIFICATION

SUMMARY

A high-level overview of various aspects of the technology disclosed herein is provided here for that reason, to provide an overview of the disclosure and to introduce a selection of concepts that are further described in the Detailed Description section below. This Summary is not intended to identify key features or essential features of the claimed subject matter, nor is it intended to be used as an aid in isolation to determine the scope of the claimed subject matter. The present disclosure is directed, in part, to systems and methods corresponding to biometric and environmental triggers for enhanced detection, stimulation, and notification, substantially as shown in and/or described in connection with at least one of the figures, and as set forth more completely in the claims.

In aspects set forth herein, and at a high level, the systems, methods, and media disclosed herein correspond to wearables (e.g., an apparel item configured for an upper torso, an apparel item configured for a lower torso, a glove, other types of wearables, or one or more combinations thereof). The wearables may have one or more biometric sensors (e.g., a heart rate sensor, a sweat sensor, a glucose sensor, other types of biometric sensors, or one or more combinations thereof) affixed thereon. The wearables may also include one or more environmental sensors (e.g., an imaging sensor, a location sensor, a toxic gas sensor, an oxygen sensor, a temperature sensor, a soundwave sensor, an electromagnetic field sensor, a radiation sensor, other types of environmental sensors, or one or more combinations thereof) affixed thereon. Additionally, the wearables may include one or more sensation devices (e.g., a visible light source, a haptic feedback device, other types of sensation devices, or one or more combinations thereof). The wearables emulate, transmogrify, or enhance one or more human senses using the one or more sensation devices based on biometric data received from the biometric sensors or environmental data received from the environmental sensors.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

BRIEF DESCRIPTION OF THE DRAWINGS

Aspects of the present disclosure are described in detail herein with reference to the attached figures, which are intended to be exemplary and non-limiting, wherein.

DETAILED DESCRIPTION

The subject matter of embodiments of the invention is described with specificity herein to meet statutory requirements. However, the description itself is not intended to limit the scope of this patent. Rather, the inventors have contemplated that the claimed subject matter might be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Throughout this disclosure, several acronyms and shorthand notations are employed to aid the understanding of certain concepts pertaining to the associated system and services. These acronyms and shorthand notations are intended to help provide an easy methodology of communicating the ideas expressed herein and are not meant to limit the scope of embodiments described in the present disclosure. The following is a list of these acronyms:

3G Third-Generation Cellular Communication System
4G Fourth-Generation Cellular Communication System
5G Fifth-Generation Cellular Communication System
6G Sixth-Generation Cellular Communication System
AOA Angle of Arrival
API Application Programming Interface
CA Carrier Aggregation
CD-ROM Compact Disk Read Only Memory
CDMA Code Division Multiple Access
DVD Digital Versatile Discs
EEPROM Electrically Erasable Programmable Read Only Memory
EMF Electromagnetic Field
eNB Evolved Node B
Ev-DO Evolution-Data Optimized
FD-MIMO Full-Dimension Multiple-Input Multiple-Output
gNB Next Generation Node B
GPRS General Packet Radio Service
GSM Global System for Mobile communications
HSS Home Subscriber System
IEEE Institute of Electrical and Electronics Engineers
IP Internet Protocol
LTE Long Term Evolution
MAC Media Access Control
MIMO Multiple-Input Multiple-Output
MME Mobility Management Entity
MU-MIMO Multi-User Multiple-Input Multiple-Output
NR New Radio
OTDOA Observed Time Difference of Arrival
PC Personal Computer
PDA Personal Digital Assistant RAM Random Access Memory
RAN Radio Access Node
RF Radio-Frequency
ROM Read Only Memory
RRC Radio Resource Control
RRU Remote Radio Unit
RSRP Reference Signal Received Power
RSRQ Reference Signal Received Quality
RSSI Received Signal Strength Indicator
RTT Round-Trip Time
TCP Transmission Control Protocol
TDMA Time Division Multiple Access
TOA Time of Arrival
UDP User Datagram Protocol
UE User Equipment
VONR Voice over NR
VOLTE Voice over LTE
WiMAX Worldwide Interoperability for Microwave Access In addition, words such as "a" and "an," unless otherwise indicated to the contrary, may also include the plural as well as the singular. Thus, for example, the constraint of "a feature" is satisfied where one or more features are present. As such, an element in the singular may refer to "one or more."

Further, the term "or" includes the conjunctive, the disjunctive, and both (a or b thus includes either a or b, as well as a and b).

In addition, the term "some" may refer to "one or more."

The term "combination" (e.g., one or more combinations thereof) may refer to, for example, "at least one of A, B, and C"; "at least two of A, B, or C" (e.g., AA, AB, AC, BB, BA, BC, CC, CA, CB); "each of A, B, and C"; and may include multiples of A, multiples of B, or multiples of C (e.g., CCABB, ACBB, ABB, etc.). Other combinations may include more or less than three options associated with the A, B, and C examples.

Unless specifically stated otherwise, descriptors such as "first," "second," and "third," for example, are used herein without imputing or otherwise indicating any meaning of priority, physical order, arrangement in a list, or ordering in any way, but are merely used as labels to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly that might, for example, otherwise share a same name.

Additionally, "user device," as used herein, is a device that has the capability of using a wireless telecommunications network, and may also be referred to as a "computing device," "mobile device," "user equipment" (UE), or "wireless communication device." A user device, in some aspects, may take on a variety of forms, such as a PC, a laptop computer, a tablet, a mobile phone, a PDA, a server, an Internet of Things device, any other device capable of communicating with other devices (e.g., by transmitting or receiving a signal) using a wireless communication, or one or more combinations thereof. A user device may be, in an embodiment, similar to user device 102 described herein with respect to FIG. 1. A user device may also be, in another embodiment, similar to user device 600, described herein with respect to FIG. 6.

As noted above, the user device may include Internet of Things devices, such as one or more of the following: a sensor (e.g., a temperature sensor), controller (e.g., a lighting controller, a thermostat), an appliance (e.g., a smart refrigerator, a smart air conditioner, a smart alarm system), other Internet of Things devices, or one or more combinations thereof. Internet of Things devices may be stationary, mobile, or both. In some aspects, the user device is associated with a vehicle (e.g., a video system in a car capable of receiving media content stored by a media device in a house when coupled to the media device via a local area network). In some aspects, the user device comprises a medical device, a location monitor, a clock, a drone, a remote weather station, another wireless communication device, or one or more combinations thereof.

In embodiments, a user device discussed herein may be configured to communicate using one or more of 4G (e.g., LTE), 5G, 6G, another generation communication system, or a combination thereof. In some aspects, the UE has a radio that connects with a 4G cell site but is not capable of connecting with a higher generation communication system. In some aspects, the UE has components to establish a 5G connection with a 5G gNB, and to be served according to 5G over that connection. In some aspects, the user device may be an E-UTRAN New Radio-Dual Connectivity (ENDC) device. ENDC allows a user device to connect to an LTE eNB that acts as a master node and a 5G gNB that acts as a secondary node. As such, in these embodiments, the ENDC device may access both LTE and 5G simultaneously, and in some cases, on the same spectrum band.

As used herein, the term "cell site" generally refers to one or more cellular base stations, nodes, RRUs control components, other components configured to provide a wireless interface between a wired network and a wirelessly connected user device, or a combination thereof. A cell site may comprise one or more nodes (e.g., eNB, gNB, other nodes, or one or more combinations thereof) that are configured to communicate with user devices. In some aspects, the cell site may include one or more band pass filters, radios, antenna arrays, power amplifiers, transmitters/receivers, digital signal processors, control electronics, GPS equipment, other equipment, or a combination thereof. A node (e.g., eNB or gNB) corresponding to the cell site may comprise one or more of a macro base station, a small cell or femtocell base station, a relay base station, another type of base station, or one or more combinations thereof. In aspects, the cell site may be configured as FD-MIMO, massive MIMO, MU-MIMO, cooperative MIMO, 3G, 4G, 5G, 6G, another generation communication system, or one or more combinations thereof. In addition, the cell site may operate in an extremely high frequency region of the spectrum (e.g., from 30 GHz to 300 GHz), also known as the millimeter band.

Embodiments of the technology described herein may be embodied as, among other things, a method, system, or computer-program product. Accordingly, the embodiments may take the form of a hardware embodiment, or an embodiment combining software and hardware. An embodiment that takes the form of a computer-program product can include computer-useable instructions embodied on one or more computer-readable media.

Computer-readable media include both volatile and nonvolatile media, removable and nonremovable media, and contemplate media readable by a database, a switch, and various other network devices. Network switches, routers, and related components are conventional in nature, as are means of communicating with the same. By way of example, and not limitation, computer-readable media comprise computer-storage media and communications media.

Computer-storage media, or machine-readable media, include media implemented in any method or technology for storing information. Examples of stored information include computer-useable instructions, data structures, program modules, and other data representations. Computer-storage media include, but are not limited to RAM, ROM, EEPROM, flash memory or other memory technology, CD-ROM, DVD, holographic media or other optical disc storage, magnetic cassettes, magnetic tape, magnetic disk storage, and other magnetic storage devices. These memory components can store data momentarily, temporarily, or permanently.

Communications media typically store computer-useable instructions-including data structures and program modules—in a modulated data signal (e.g., a modulated data signal referring to a propagated signal that has one or more of its characteristics set or changed to encode information in the signal). Communications media include any information-delivery media. By way of example but not limitation, communications media include wired media, such as a wired network or direct-wired connection, and wireless media such as acoustic, infrared, radio, microwave, spread-spectrum, and other wireless media technologies. Combinations of the above are included within the scope of computer-readable media.

By way of background, prior computing systems, such as smart watches, for example, merely detected steps taken within a period of time using an accelerometer. Additionally, prior systems, such as the smart watch, do not incorporate other sensors, such as a thermometer or a radiation detector, for example. Furthermore, these prior systems have no way to emulate or enhance human senses themselves; rather, these smart watches merely detect and display results based on the data received (such as the steps detected by the accelerometer). At best, a cell phone merely rings or vibrates based on a received message or phone call. A phone that is merely ringing in response to receiving a message or phone call does not emulate or enhance human sense, especially when the cell phone is not within a particular range of the recipient.

The technology discussed herein can alleviate the problems and shortcomings discussed above. For instance, embodiments disclosed herein provide for biometric apparel systems that emulate or enhance one or more human senses, using one or more sensation devices affixed to a biometrics apparel item, based on biometric data received by one or more biometric sensors affixed to the apparel item and environmental data received by one or more environmental sensors affixed to the apparel item.

In one aspect, a biometrics apparel system comprises an apparel item, the apparel item comprising at least a front portion and a back portion. The system also comprises one or more biometric sensors affixed to the apparel item for receiving biometric data. One or more environmental sensors are also affixed to the apparel item for receiving environmental data. Additionally, one or more sensation devices are affixed to the apparel item. As such, the biometrics apparel system transmogrifies one or more human senses using the one or more sensation devices based on the biometric data received by the one or more biometric sensors and the environmental data received by the one or more environmental sensors.

In another aspect, a method for utilizing a biometrics apparel item is provided. The method comprises receiving, from one or more environmental sensors affixed to the biometrics apparel item, environmental data and determining that the environmental data received from the one or more environmental sensors is above a threshold. Based on the environmental data being above the threshold, a signal is generated via one or more sensation devices. As such, the biometrics apparel item transmogrifies one or more human senses using the one or more sensation devices affixed to the biometrics apparel item.

In yet another aspect, a system is provided for operating a biometrics apparel item. The system comprises one or more processors and one or more computer storage memory having computer-executable instructions stored thereon that, when executed by the one or more processors, cause the system to perform operations. The operations comprise receiving, from one or more biometric sensors affixed to the biometrics apparel item, biometric data. The system determines that the biometric data received from the one or more biometric sensors is above a threshold. Based on the biometric data being above the threshold, the system causes the biometrics apparel item to generate a haptic feedback signal via one or more sensation devices affixed to the apparel item, wherein the biometrics apparel item transmogrifies one or more human senses based on receiving the biometrics data.

Figure 1:
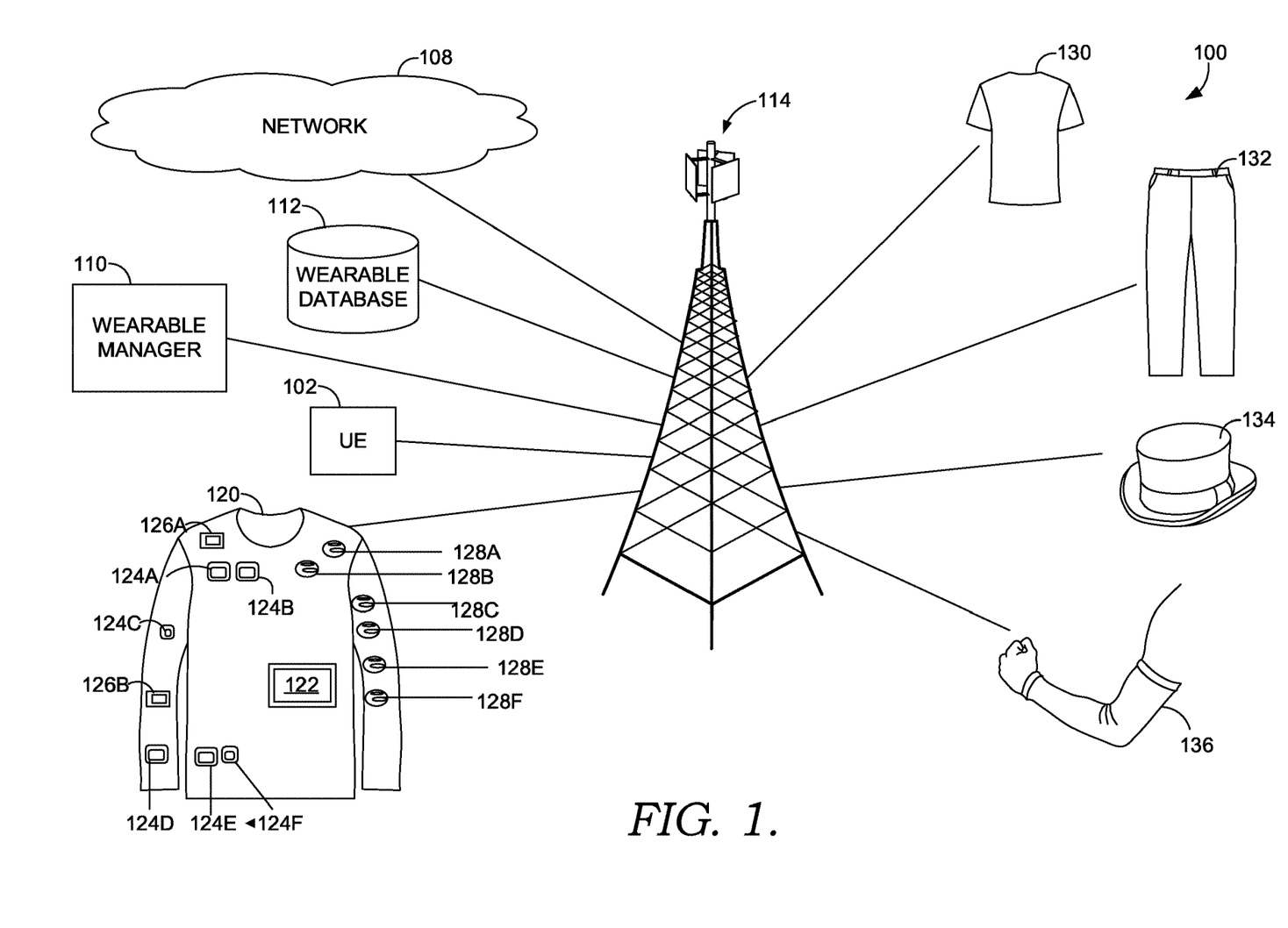
FIG. 1 depicts an example environment corresponding to biometric and environmental triggers for enhanced detection, stimulation, and notification, in accordance with embodiments herein.

Turning now to FIG. 1, example environment 100 comprises user device 102, network 108, wearable manager 110, wearable database 112, cell site 114, and wearables 120, 130, 132, 134, and 136. Wearable 120 in example environment 100 is a biometrics apparel item configured for an upper torso, wearable 130 is another biometrics apparel item configured for an upper torso, wearable 132 is a biometrics apparel item configured for a lower torso, wearable 134 is a biometrics apparel item configured for a head, and wearable 136 is a biometrics apparel item configured for an arm. Wearable 120 comprises a control unit 122; a plurality of biometric sensors 124A, 124B, 124C, 124D, 124E, 124F; a plurality of environmental sensors 126A, 126B; and a plurality of sensation devices 128A, 128B, 128C, 128D, 128E, 128F. Example environment 100 is but one example of a suitable environment for biometric and environmental triggers for enhanced detection, stimulation, and notification, and is not intended to suggest any limitation as to the scope of use or functionality of the invention. Neither should the environment 100 be interpreted as having any dependency or requirement relating to any one or combination of components illustrated.

As depicted by example environment 100, user device 102 (as well as additional user devices) may wirelessly communicate via network 108. User device 102 can communicate using one or more wireless communication standards. For example, the user device 102 may be configured to communicate using a wireless networking (e.g., Wi-Fi) or one or more peer-to-peer wireless communication protocols (e.g., Bluetooth, Wi-Fi peer-to-peer, other peer-to-peer protocols, or one or more combinations thereof) in addition to at least one cellular communication protocol (e.g., GSM, UMTS (associated with WCDMA or TD-SCDMA air interfaces, for example), LTE, LTE-A, 5G NR, HSPA, 3GPP2 CDMA2000 (e.g., 1×RTT, 1×EV-DO, HRPD, eHRPD), other cellular communication protocols, or one or more combinations thereof). The user device 102 may additionally or alternatively communicate using one or more global navigational satellite systems (GNSS, such as GPS or GLONASS for example), one or more mobile television broadcasting standards (e.g., ATSC-M/H or DVB-H), another wireless communication protocol, or one or more combinations thereof. In some embodiments, the user device 102 may include separate transmit or receive chains (e.g., including separate antennas and other radio components) for each wireless communication protocol with which it is configured to communicate. The user device 102 can also communicate with the wearables 120, 130, 132, 134, and 136 via the network 108.

The telecommunications network 108, for example, may provide one or more communication services. The one or more communication services may include, for example, the transfer of information without the use of an electrical conductor as the transferring medium. A wireless communication service may correspond to the transfer of information via radio waves (e.g., Bluetooth®), satellite communication, infrared communication, microwave communication, Wi-Fi, millimeter wave communication, mobile communication, another type of communication, or a combination thereof. In embodiments, the communication service may include one or more of a voice service, a message service (e.g., SMS messages, MMS messages, instant messaging messages, an EMS service messages), a data service, other types of wireless telecommunication services, or a combination thereof. In embodiments, the one or more communication services may be provided by one or more communication providers. For example, a user device may correspond to a user who is registered or subscribed to a communication service provider to utilize one or more communication services.

The telecommunications network 108 may correspond to one or more of 3G, 4G, 5G, 6G, another generation communication system, 802.11, millimeter waves, FD-MIMO, massive MIMO, MU-MIMO, cooperative MIMO, another type of communication system, or one or more combinations thereof. Additionally, other wireless communication protocols may be utilized in conjunction with aspects described herein. For example, embodiments of the present technology may be used with one or more wireless communication protocols or standards, including, but not limited to, CDMA 1× Advanced, GPRS, Ev-DO, TDMA, GSM, WiMAX technology, LTE, LTE Advanced, other technologies and standards, or a combination thereof.

In embodiments, one or more cell sites 114 provide the one or more wireless communication services via network 108, the network 108 comprising one or more telecommunication networks, or a portion thereof. A telecommunication network might include an array of devices or components (e.g., one or more cell sites 114). The network 108 can include multiple networks, and the network can be a network of networks. In embodiments, the network 108 is a core network, such as an evolved packet core, which may include at least one MME, at least one serving gateway, and at least one Packet Data Network gateway. The MME may manage non-access stratum (e.g., control plane) functions such as mobility, authentication, and bearer management for other devices associated with the evolved packet core. In an embodiment, the network 108 comprises at least two core networks associated with a legacy LTE network and a 5G network. The at least two core networks may each operate one or more public land mobile networks, which may operate in each of the at least two core networks (e.g., one public land mobile network operates in each of an evolved packet core and a 5G core network). In embodiments, different core networks may be provided for different types of services, for different types of customers, for different types of traffic, to provide different levels of Quality of Service, or one or more combinations thereof. The network 108 can comprise any communication network providing voice, message, or data service(s), such as, for example, a 1× circuit voice, a 3G network (e.g., CDMA, CDMA2000, WCDMA, GSM, UMTS), a 4G network (WiMAX, LTE, HSDPA), a 5G network, a 6G network, another generation network, or one or more combinations thereof.

Components of the network 108, such as terminals, links, and nodes (as well as other components), can provide connectivity in various implementations. For example, components of the network 108 may include core network nodes, relay devices, integrated access and backhaul nodes, macro eNBs, small cell eNBs, gNBs, relay cell sites, other network components, or a combination thereof. The network 108 may interface with one or more cell sites through one or more wired or wireless backhauls. As such, the one or more cell sites 114 may communicate to the user device 102 and the wearables 120, 130, 132, 134, 136 via the network 108 or directly. Furthermore, user devices can utilize the network 108 to communicate with other devices (e.g., a user device(s), a server(s), etc.) through the one or more cell sites 114.

The one or more cell sites 114 may include one or more cells, band pass filters, radios, antennas, antenna arrays, power amplifiers, transmitters/receivers, digital signal processors, control electronics, GPS equipment, and the like. In some aspects, the cell site 114 may comprise one or more macro cells (providing wireless coverage for users within a large geographic area). For example, macro cells may correspond to a coverage area having a radius of approximately 1-15 miles or more, the radius measured at ground level and extending outward from an antenna at the cell site. In some aspects, cell site 114 may comprise, or be in communication with, one or more small cells (providing wireless coverage for users within a small geographic area). For example, a small cell may correspond to a coverage area having a radius of approximately less than three miles, the radius measured at ground level and extending outward from an antenna at the cell site. In embodiments, cell site 114 is in communication with a plurality of in-door small cells.

Furthermore, the one or more small cells may support low frequency communications via low frequency nodes or millimeter waves (mmWaves) via mmWave nodes, corresponding to an antenna. Additionally, the one or more small cells may combine a plurality of 100 MHz channels. Continuing the example, the one or more small cells may also combine radio and antenna elements. Further, the one or more small cells may each have an Ethernet cable backhaul. Additionally, the one or more small cells may have the capability of transferring data to multiple user devices during a single point in time via a plurality of antennas (e.g. via a multi-user MIMO antenna system). In some embodiments, network 108 includes both the one or more small cells and the one or more macro cells (known as a heterogeneous network). A heterogeneous network may include Home eNBs, which may provide service to a closed subscriber group.

Wearable manager 110 may include one or more servers for managing biometric data and environmental data received from biometric sensors and environmental sensors affixed to the wearables 120, 130, 132, 134, 136. For example, wearable manager 110 can retrieve biometric data and environmental data stored at wearable database 112. Continuing the example, the wearable manager 110 can compare real-time data or near real-time data received to data stored at the wearable database 112. In some embodiments, wearable manager 110 can store data in the wearable database 112 based on user profiles comprising personal user information. The personal user information can include a first and last name, prior health histories, diet information, height, weight, activity level history, as well as other personal user information. Additionally, the personal user information may include the type of the wearable (e.g., a biometric apparel item configured for an upper torso or lower torso). The data stored at the wearable database 112 may include time and date stamps provided by the wearable manager 110.

As noted above, the wearable 120 comprises a control unit 122 (discussed further with reference to FIG. 5); a plurality of biometric sensors 124A, 124B, 124C, 124D, 124E, 124F; a plurality of environmental sensors 126A, 126B; and a plurality of sensation devices 128A, 128B, 128C, 128D, 128E, 128F. In embodiments, the wearables 130, 132, 134, 136 comprise one or more biometric sensors, one or more environmental sensors, one or more sensation devices, or one or more combinations thereof. Each of the sensors and sensation devices may be electrically coupled via one or more wires. The sensors and sensation devices may be an external wearable, portable, a static device, or one or more combinations thereof. In some embodiments, the sensors and sensation devices are wirelessly communicating with control unit 122. Data from the biometric sensors, environmental sensors, other sensors, and the sensation devices can be stored at the wearable database 112. Data and functionality corresponding to the biometric sensors, environmental sensors, other sensors, and the sensation devices can be managed by control unit 122.

Wearables, in some embodiments, include eyeglasses, spectacles, sunglasses, goggles, helmets, or other types of head mounted display devices. In some embodiments, wearables include socks, gloves, shirts, shorts, shoes, swimming attire, or other types of apparel. In some embodiments, the biometric sensors are affixed to the inner-facing surface of an apparel item, such that the biometric sensors are in contact with the skin of a wearer. In some embodiments, the environmental sensors are affixed to the outer-facing surface of the apparel item, such that the environmental sensors are in contact with the environment external to the body of the wearer. In some embodiments, the biometric sensors are affixed to the bridge of a pair of glasses, such that the biometric sensors are in contact with a portion of the nose of the wearer. In some embodiments, the control unit 122 is a device that is physically separate from the wearable.

The plurality of biometric sensors 124A, 124B, 124C, 124D, 124E, 124F receive biometric data. For example, the biometric sensors 124A, 124B, 124C, 124D, 124E, 124F can comprise a heart rate sensor. For example, the heart rate sensor may include a plurality of electrodes affixed to an inner-facing surface of the biometrics apparel item configured for a lower torso area or an upper torso area. In some embodiments, the electrodes are positioned on the inner-facing surface, such that the electrodes are adjacent to the skin of a wearer at or around an area between the right and left lung of the wearer. In some embodiments, one or more electromyography (EMG) sensors are affixed to an inner-facing surface of a glove biometrics apparel item or to an inner-facing surface of a sleeve portion of an upper torso apparel item. In embodiments, the heart rate sensors continuously monitor a heart rate of the wearer and periodically transmit the heart rate data to the wearable database 112. Each of the heart rate sensors are connected to or wirelessly communicating with the control unit 122 and the sensation devices 128A, 128B, 128C, 128D, 128E, 128F. In some embodiments, the biometric data received by the biometric sensors 124A, 124B, 124C, 124D, 124E, 124F and stored at wearable database 112 may include a pulse rate, an oxygen saturation, a blood pressure, or one or more combinations thereof.

In some embodiments, biometric sensors 124A, 124B, 124C, 124D, 124E, 124F may include an accelerometer. For example, a plurality of accelerometers may be affixed to a leg portion of a biometrics apparel item configured for a lower torso area or a sleeve portion of a biometrics apparel item configured for an upper torso area for detecting a rate at which a wearer is running or lifting weights, for example. In embodiments, the accelerometer sensors continuously periodically transmit accelerometer data to the wearable database 112. Each of the accelerometer sensors are connected to or wirelessly communicating with the control unit 122 and the sensation devices 128A, 128B, 128C, 128D, 128E, 128F. In some embodiments, the biometric data received by the biometric sensors 124A, 124B, 124C, 124D, 124E, 124F and stored at wearable database 112 may include a walking speed and duration, an amount of idle time, a running speed and duration, or one or more combinations thereof.

In some embodiments, biometric sensors 124A, 124B, 124C, 124D, 124E, 124F may include a glucose sensor. For example, the glucose sensor may measure a concentration of glucose via a wearer's sweat via an electrode comprising nickel. As another example, the glucose sensor may measure the concentration of glucose (e.g., mg/dL) by using an infrared light and temperature detector. In yet another example, the glucose sensor may measure a blood glucose level using radio frequencies (e.g., between 0.5 and 20 GHz). In embodiments, the one or more glucose sensors continuously periodically transmit glucose data to the wearable database 112. Each of the glucose sensors are connected to or wirelessly communicating with the control unit 122 and the sensation devices 128A, 128B, 128C, 128D, 128E, 128F. In embodiments, the control unit 122 may determine a glucose concentration and a corresponding amount of idle time based on the biometric data from the glucose sensor and the accelerometer.

In some embodiments, biometric sensors 124A, 124B, 124C, 124D, 124E, 124F may include a sweat sensor. For example, the sweat sensor may detect a sodium concentration, potassium concentration, calcium concentration, a neuropeptide concentration, a metabolite concentration (e.g., glutamic acid, aspartic acid, lactic acid, glycerol, a peptide, another type of metabolite, or one or more combinations thereof), electrolytes (e.g., sodium, potassium), other types of sweat data, or one or more combinations thereof. In some embodiments, the sweat sensor may detect a pH level. In some embodiments, the sweat sensor includes one or more ion-sensitive electrodes. In some embodiments, the sweat sensor comprises an ethanol perspiration sensor for determining an alcohol concentration. In embodiments, the one or more sweat sensors continuously periodically transmit sweat data (e.g., the neuropeptide concentration or the alcohol concentration) to the wearable database 112. Each of the sweat sensors are connected to or wirelessly communicating with the control unit 122 and the sensation devices 128A, 128B, 128C, 128D, 128E, 128F. In embodiments, the control unit 122 may determine a sodium concentration, potassium concentration, calcium concentration, a neuropeptide concentration, alcohol concentration, or pH level and a corresponding amount of idle time based on the biometric data from the sweat sensor and the accelerometer. In embodiments, the control unit 122 may determine a hunger level or dehydration level using the sweat sensor, the glucose sensor, the accelerometer sensor, the heart rate sensor, or one or more combinations thereof.

In some embodiments, the environmental sensors 126A, 126B affixed to their corresponding apparel item may be used for emulating or enhancing a wearer's senses based on the environment around the wearer of the corresponding wearable. For example, if the wearer of the wearable is blind, the environmental sensors may include location sensors and imaging sensors for guiding the wearer as the wearer is walking (e.g., by generating haptic feedback signals via the sensation devices based on objects in the wearer's environment). In some embodiments, the environmental sensors are affixed to a first sleeve portion of an apparel item configured for an upper torso, a first leg portion of an apparel item configured for a lower torso, or one or more combinations thereof. In some embodiments, the environmental sensors are affixed to a shoulder region or chest region of the apparel item configured for the upper torso. In some embodiments, the environmental sensors are coupled to an exterior portion of a shoe (e.g., the laces, an outsole, the heel, the toe cap).

The location sensors, for example, can obtain location data by way of MIMO communication, Bluetooth Low Energy protocol, radio frequency signaling, and other communication technologies. In some embodiments, the location data may include a distance between the wearable 120 (or wearables 130, 132, 134, 136) and another associated device (e.g., a user device, a smart TV, another wearable). In some embodiments, the wearables 120, 130, 132, 134, 136 may determine the distance from another device by using a Bluetooth Low Energy beacon radio signal strength identifier over time or an inertial measurement unit change. In some embodiments, the location data may include one or more of a latitude, a longitude, an elevation or altitude, or a combination thereof. The elevation or altitude may be determined using altitude sensor (e.g., an altimeter), a pressure sensor, or one or more combinations thereof, for example. Further, the location data may include an associated timestamp.

The location data, in some embodiments, may include GPS location data, Wi-Fi location data, manually-entered location data from a corresponding user device, or one or more combinations thereof. The location data may be obtained via triangulation of an RSSI received by the cell site 114, an RSSI received by a Wi-Fi router, an RSSI received by the cell site 114, or one or more combinations thereof. In some embodiments, the location data is obtained based on cell site 114 communications using GPS satellite triangulation, Bluetooth triangulation, other triangulation techniques (e.g., using two or more gNBs), or one or more combinations thereof. The location data may also include a distance between an antenna associated with the cell site 114 and the wearables 120, 130, 132, 134, 136; a measured time difference between reference signals transmitted by the cell site 114; or one or more combinations thereof. In aspects, the location data may be a set of coordinates relative to a known location defined by geographic or civic (e.g., a postal address) terms.

In embodiments, the cell site 114 may determine the location of the wearables 120, 130, 132, 134, 136 by using a 5G network (e.g., NG Radio Access Networking and a 5G Core Network) and OTDOA positioning. In some embodiments, the location data is determined using a Global Navigation Satellite System satellite vehicle. In some embodiments, the location data is determined using position reference signals transmitted by the cell site 114. In some embodiments, the location data is determined based on a combination of one or more of GPS coordinates, propagation times, signal strengths, directional information associated with a beam of the cell site 114, and so forth.

In some aspects, the location data is determined by a server (e.g., wearable manager 110) based on the wearables 120, 130, 132, 134, 136 reporting location measurements. For example, the server may store antenna location information, radio beam direction information, antenna pattern information, bound geographic area information, other location information associated with a cell or radio beam corresponding to the cell site 114, or one or more combinations thereof. In some embodiments, the server determines the location of the cell site 114 based on location measurements received from the cell site 114, from the wearables, or from a corresponding UE. For example, the location measurements may comprise RSSI, RTT, RSRP, RSRQ, AOA, TOA, other signals transmitted by a wearable, or a combination thereof.

In embodiments, the imaging sensor is capable of receiving image data. For example, the imaging sensor can capture one or more digital images (e.g., one or more still images, one or more sequences of images, video frames, other image types, or one or more combinations thereof). In some embodiments, for example, the imaging sensor may include an optical character recognition sensor, an x-ray imaging sensor, a 3-D imaging sensor, an ultrasonic sensor (e.g., a proximity sensor), another type of imaging sensor, or one or more combinations thereof. For example, the imaging sensor comprising the proximity sensor may receive data corresponding to objects within a threshold distance from the wearable 120, 130, 132, 134, 136.

In some embodiments, the imaging sensors may perform focusing techniques (e.g., by using a range sensor). Image data from the imaging sensors may include pixel data, focus data, or one or more combinations thereof. Further, an imaging sensor on the wearables 120, 130, 132, 134, 136 may include a plurality of imaging sensors. For example, an imaging sensor may include an array of pixels comprising imaging pixels. In some embodiments, the array of pixels also includes focus pixels. The imaging pixel data may be based on signals from imaging pixels, and focus pixel data of the image data may be based on signals from the focus pixels. In some embodiments, the array of pixels includes an array of photodiodes (e.g., photodiodes of focus pixels).

In some embodiments, the imaging sensors are sensors that detect and convey image data for generating an image. One or more of the imaging sensors may comprise an active-pixel sensor, a complementary metal oxide semiconductor imaging sensor, an N-channel metal oxide semiconductor imaging sensor, a P-channel metal oxide semiconductor imaging sensor, a dynamic vision sensor, a charge-coupled device imaging sensor, an optical character recognition sensor, a programmable gain amplifier, a range sensor, a thermal imaging sensor, a radar sensor, an ultrasonic sensor, an mmWaves radar sensor, another type of imaging sensor, or one or more combinations thereof.

An imaging sensor may be capable of capturing images in a file format, such as Joint photographic experts group (JPEG), Graphics interchange format (GIF), Standards for bitmap (BMP), Tagged image file format (TIFF), another type of file format usable for images (e.g., some of which may be converted to a different format before processing the image), or one or more combinations thereof. As such, the image data may be stored in the wearable database 112 as JPEG, GIF, BMP, TIFF, another format usable for images, or one or more combinations thereof. In some embodiments, the biometric data is stored in a memory of the control unit 122 (e.g., memory 504 of FIG. 5). In embodiments, one or more of the imaging sensors include an image processor.

In embodiments, the environmental sensors (e.g., environmental sensors 126A, 126B) of a wearable (e.g., wearables 120, 130, 132, 134, 136) may include a soundwave sensor or an electromagnetic field sensor. For example, the environmental sensors may include a microphone, a high frequency radio sensor, an ultraviolet sensor, an ultrasound sensor, an infrared sensor, an x-ray sensor, a gamma ray sensor, a microwave sensor, another type of soundwave or electromagnetic wave sensor, or one or more combinations thereof. Each of the soundwave sensors or electromagnetic wave sensors are connected to or wirelessly communicating with the control unit 122 and the sensation devices 128A, 128B, 128C, 128D, 128E, 128F. In embodiments, the control unit 122 may determine an ultraviolet level, an infrared level, an x-ray level, a gamma ray level, a microwave level, or another type of sound or electromagnetic wave level is above a threshold. Additionally, the control unit 122 can determine a corresponding amount of time within an area having the sound or electromagnetic wave level above the threshold.

In some embodiments, the EMF sensor comprises an antenna fabricated using photolithographic techniques on a printed circuit board (e.g., a 5 mm×5 mm square printed on a circuit board). In some embodiments, the ultraviolet sensor comprises one or more radiometers capable of measuring instantaneous ultraviolet wavelength intensity, or one or more dosimeters capable of measuring accumulated ultraviolet light over time. Using the ultraviolet sensor, the control unit 122 or the corresponding user device 102 can provide a radiometric readout of an ultraviolet index based on weighting photons according to an erythema action spectrum. In some embodiments, the ultraviolet sensor has one or more ultraviolet sensors coupled with an amplifier, an analog-to-digital converter, a microcontroller, another type of electronic, or one or more combinations thereof. In some embodiments, the ultraviolet sensor comprises one or more photodiodes. In some embodiments, the electromagnetic wave sensor or sound sensor comprises a filter for determining relative proportions of a particular wavelength received by the corresponding sensor. In some embodiments, the electromagnetic wave sensor or sound sensor comprises a diffuser having a cosine response and that collects an array of detectable wavelengths and transmits the array uniformly to the filter.

In some embodiments, the ultrasound sensor comprises an ultrasound emitter and receiver. The ultrasound sensor may measure a change in ultrasound pressure as a function of distance between the emitter and the receiver. In some embodiments, the infrared sensor can detect infrared radiation in the environment around the wearer of the wearable 120, 130, 132, 134, 136. In some embodiments, the infrared sensor can detect wavelengths within a range of 780 nm to 50 µm. In some embodiments, the infrared sensor can detect these wavelengths within a predetermined angle range. Additionally, the infrared sensor, in some embodiments, can detect a change in the concentration of these wavelengths over a period of time (e.g., based on movements of the wearer or movements within the environment of the wearer, such as cars or people). In some embodiments, the infrared sensor uses wavelengths from 2 µm to 14 µm to detect the infrared wavelengths.

In some embodiments, the x-ray sensor can use an electric current to measure received x-rays. For example, an incoming x-ray interacts with one or more materials of the x-ray sensor, frees one or more electrons associated with the material being interacted with, and the free electrons can be measured via an electric field of the sensor. In some embodiments, the x-rays sensor comprises a microchannel plate or a semiconductor chip. In embodiments, the environmental sensors (e.g., environmental sensors 126A, 126B) of a wearable (e.g., wearables 120, 130, 132, 134, 136) may include a radiation sensor (e.g., a gamma ray sensor). The radiation sensor may include a scintillation, a cadmium zinc telluride sensor, another type of radiation sensor, or one or more combinations thereof. In some embodiments, the control unit 122 includes radiation spectroscopy software for determining isotopes and levels of radiation in the environment of the wearer of the wearable 120, 130, 132, 134, 136. In some embodiments, the radiation spectroscopy software includes a radioisotope library (e.g., based on ANSI, international standards, industry standards). In some embodiments, the radiation sensor can detect gamma neutrons. In some embodiments, the radiation sensor includes a microwave sensor comprising electromagnetic absorption material, material for converting electromagnetic waves to heat, and a material that converts the heat into electrical resistance.

In embodiments, the environmental sensors (e.g., environmental sensors 126A, 126B) of a wearable (e.g., wearables 120, 130, 132, 134, 136) may include oxygen sensor, a toxic gas sensor, a combustible gas sensor, a smoke sensor, another type of gas sensor, or one or more combinations thereof. In embodiments, the oxygen sensors can measure a concentration of oxygen in the environment of the wearer of the corresponding wearable. The control unit 122 or user device 102 may determine when the oxygen concentration in the environment is below a threshold level. The oxygen sensor may comprise an electronic sensor, an electrochemical sensor (e.g., galvanic cell), a microprocessor, an analog to digital converter, pressure sensor, or one or more combinations thereof. In some embodiments, the environmental sensor includes a nitrogen oxide sensor for detecting the concentration of nitrogen oxide in the air. In some embodiments, the environmental sensor can detect ammonia gas (e.g., 50 ppm), carbon dioxide (e.g., via an infrared detector), carbon monoxide (e.g., 500 ppm), hydrogen sulfide (e.g., 50 ppm), methane gas, chlorine gas (e.g., 10 ppm), formaldehyde gas (e.g., 10 ppm), hydrogen gas, nitric oxide, nitrogen dioxide, other types of toxic or combustible gases, or one or more combinations thereof.

In some embodiments, the environmental sensors comprise a temperature or humidity sensor. For example, an active or passive RFID tag may be used for detecting a temperature or humidity level. For instance, the Matrics Group MicroSensys™ active RFID tags and KSW Microtec Smart Active Label™ active RFID tags include temperature sensors. In some embodiments, the temperature sensor can measure an ambient temperature. In some embodiments, a circuitry on the RFID tag may include reference information about the temperature. For example, the RFID tag of a wearable may be programmed (e.g., via a corresponding application on the user device 102) to a particular temperature range, the RFID tag and corresponding biometrics apparel item will determine if the temperature of the environment of the wearer is outside of the particular temperature range. In embodiments, the active RFID tag may also periodically record temperatures over time.

In embodiments, the sensation devices (e.g., sensation devices 128A, 128B, 128C, 128D, 128E, 128F) of a wearable (e.g., wearables 120, 130, 132, 134, 136) may include one or more of piezoelectric actuators, one or more eccentric rotating mass motors, one or more of linear resonance actuators, or one or more combinations thereof for generating haptic feedback signals (e.g., mechanical vibrations, features changes to an inner-surface of an apparel item (e.g., temperature or texture), changes in surface tension of the inner-surface of the apparel item, electric pulses, another type of stimuli that can be perceived through non-visual, touch-based senses, or one or more combinations thereof). In some embodiments, the sensation devices generate a series of tactile feedback responses based on the biometric data received by the one or more biometric sensors and the environmental data received by the one or more environmental sensors. The types of the series of tactile feedback responses may be the same or different types of haptic feedback signals. In embodiments, a haptic feedback signal can include a waveform, which can include a sinusoidal wave, a square wave, a triangle wave, a sawtooth wave, a pulse wave, another type of periodic or non-periodic wave, or one or more combinations thereof.

In embodiments, the sensation devices may additionally or alternatively include a plurality of visible light sources affixed to an outer-facing surface of the biometrics wearable, such that the plurality of visible light sources generate visible light based on the biometric data, the environmental data, or one or more combinations thereof. For example, a biometrics apparel item may include the plurality of visible light sources affixed to the outer-facing surface of a leg portion, an arm portion, a chest region, a back portion, a waist portion, a palm portion, another body portion, or one or more combinations thereof. In some embodiments, the plurality of visible light sources may generate one or more wavelengths of visible light based on the environmental data from the active or passive RFID tag, the gas sensor, the electromagnetic wave sensor, another environmental sensor, or one or more combinations thereof.

Figure 2:
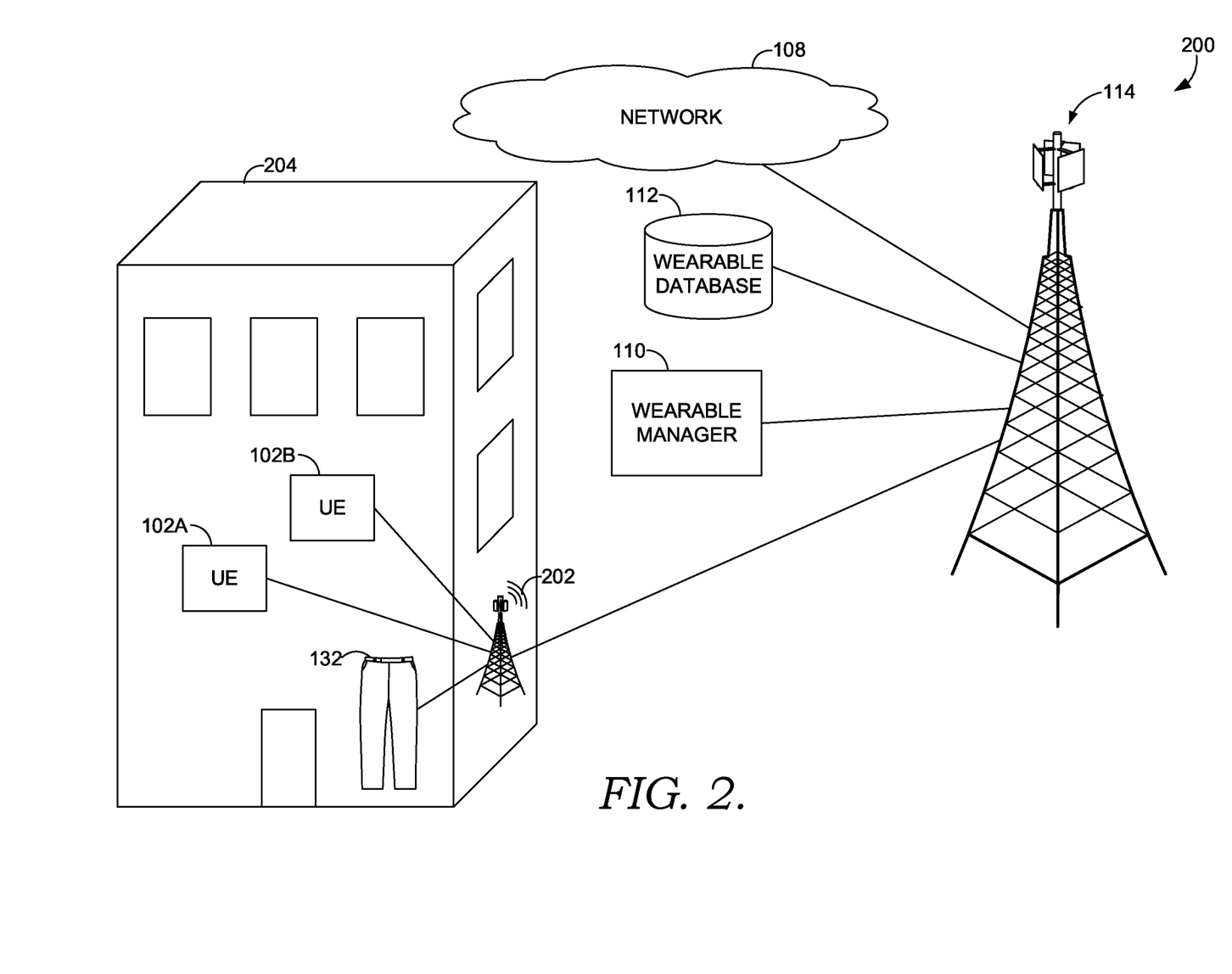
FIG. 2 illustrates another example environment corresponding to indoor communications with biometric apparel systems and user devices, in accordance with embodiments herein.

FIG. 2 illustrates example environment 200 corresponding to indoor communications with biometric apparel systems and user devices. Example environment 200 comprises user devices 102A, 102B (e.g., user device 102 of FIG. 1 or user device 600 of FIG. 6), network 108 (described above with respect to FIG. 1), wearable manager 110, wearable database 112, cell site 114, access point 202, enclosed area 204 (e.g., a building or a stadium in other embodiments), and wearable 132. Example environment 200 is but one example of a suitable environment for indoor communications with biometric apparel systems and user devices, and is not intended to suggest any limitation as to the scope of use or functionality of the invention. Neither should the environment 200 be interpreted as having any dependency or requirement relating to any one or combination of components illustrated.

Turning to access point 202, cell site 114 may be in communication with one or more access points 202 located in an enclosed area 204 (e.g., in a commercial or residential building). In some embodiments, the access point 202 comprises one or more small cells (e.g., femtocell, Picocell, metro cell, other types of small cells, or one or more combinations thereof) that can support indoor communications via one or more access nodes, such as mmWave nodes (e.g., mmWave 5G), for example. Additionally, the one or more small cells may combine a plurality of 100 MHz channels. Continuing the example, the access point 202 may also combine radio and antenna elements. Further, the one or more small cells of access point 202 may each have an Ethernet cable backhaul. Additionally, the one or more small cells of access point 202 may have the capability of transferring data to multiple user devices during a single point in time via a plurality of antennas (e.g. via a multi-user MIMO antenna system). The one or more small cells of access point 202 may also comprise one or more antennas, a radio, a controller, or one or more combinations thereof. Furthermore, the one or more small cells of access point 202 can communicate with UEs 102A, 102B and wearable 132 (as well as other UEs and other wearables) that are within the enclosed area 204. The one or more small cells of access point 202 can provide one or more protocols (e.g., 3G, 4G, 5G, and additional generation networks) via one or more providers.

Furthermore, cell site 114 and access point 202 may be in communication via a backhaul. The backhaul may be wired or wireless, and may comprise dark fiber for 5G communication services, for example. In aspects, the backhaul may be connected via wireless links to a section of the network 108, and also connected via a wire to another section of the network 108. The backhaul may be fully integrated with 5G NR access via a plurality of nodes (e.g., macro sites at rooftops and towers, as well as street sites at poles and walls). In embodiments, the network 108 may utilize multi-hop backhauling with the same or different frequency bands. Continuing the example, the multi-hop backhauling is a distributed routing scheme in a small cell of access point 202 can form a neighbor relationship with other connected small cells. In other embodiments, the backhaul may include a multi-path and multi-hop architecture in the mmWave frequency band.

In embodiments, the access point 202 can periodically and repeatedly transmit one or more frequencies. Based on the UEs 102A, 102B and wearable 132 detecting the one or more frequencies, the UEs 102A, 102B and wearable 132 can transmit an indication to the access point 202. Based on the indication transmitted to the access point 202, the access point 202 can transmit a signal to the UEs 102A, 102B and wearable 132. As such, the UEs 102A, 102B and an interface associated with the wearable 132 (e.g., an interface affixed to the wearable or an interface of an associated UE) can display a message received from the access point 202. For example, the message can include information associated with the time of the received message and associated with the enclosed area 204. In another example, the access point 202 can identify the UEs 102A, 102B and wearable 132 based on one or more transmitters of the UEs within the enclosed area 204. Continuing the example, the environmental sensors of the wearable 132 can detect environmental data comprising radioactive data or gas data from the radioactive sensors and toxic or combustive gas sensors. As such, the wearable 132 (e.g., and other wearables) can transmit the radioactive data or gas data to the access point 202. Based on the access point receiving this data, the access point 202 can transmit the message indicating a warning to each of the detected UEs or other wearables, wherein the warning is associated with the radioactive data, gas data, or one or more combinations thereof. In some embodiments, upon detection of the radioactive environmental data detected by the radioactive sensor, the wearable can provide haptic feedback signals to the wearer in addition to the warning. In some embodiments, upon detection of combustible or toxic gas environmental data detected by the gas sensor, the wearable can provide haptic feedback signals to the wearer in addition to the warning.

Figure 3:
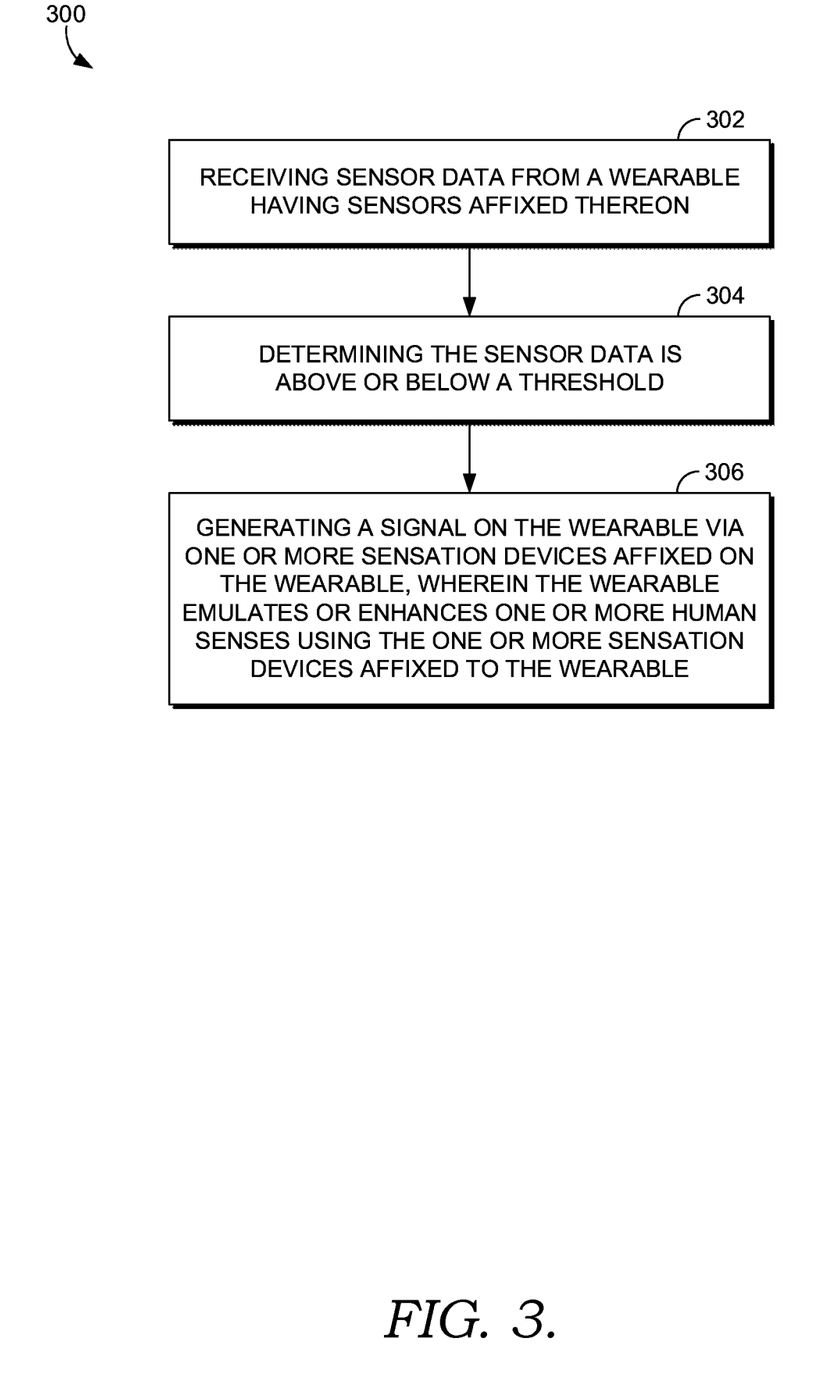
FIG. 3 depicts a flow diagram of an example method for utilizing biometric and environmental triggers for enhanced detection, stimulation, and notification, in accordance with aspects herein.

FIG. 3 depicts example method 300 for utilizing biometric and environmental triggers for enhanced detection, stimulation, and notification. At 302, sensor data is received from sensors affixed to a wearable. The wearable may include eyeglasses, spectacles, sunglasses, goggles, helmets, or other types of head mounted display devices. In some embodiments, the wearable may include socks, gloves, shirts, shorts, shoes, swimming attire, or other types of apparel. In some embodiments, the sensors are affixed to an inner-facing surface of an apparel item, such that the sensors are in contact with the skin of a wearer. In some embodiments, one or more sensors may comprise a skin patch. In some embodiments, the sensors are affixed to an outer-facing surface of the apparel item.

The sensors may include one or more biometric sensors, one or more environmental sensors, or one or more combinations thereof. For example, one or more biometric sensors may be affixed to an apparel item for receiving biometric data. As another example, one or more environmental sensors may be affixed to the apparel item for receiving environmental data. The one or more biometric sensors may include a heart rate monitor sensor, for example. As another example, the one or more biometric sensors may include a glucose sensor. In yet another example, the one or more biometric sensors may include a sweat sensor for detecting sweat data. In some embodiments, the one or more biometric sensors comprise an ethanol perspiration sensor.

The one or more environmental sensors, in an embodiment, comprise an imaging sensor and a location sensor. The imaging sensor may be affixed to a first sleeve portion of the apparel item, for example. In some embodiments, the environmental sensor includes one or more high frequency radio sensors that receive high frequency electromagnetic waves. In some embodiments, a high frequency radio wave is detected within a particular range. In some embodiments, the high frequency radio sensor is a radio frequency proximity sensor, a seismometer, another type of EMF sensor, or one or more combinations thereof. In some embodiments, a high frequency radio wave is detected when the radio wave is above or below a threshold. In some embodiments, the one or more environmental sensors comprise an ultrasonic sensor (e.g., that can detect frequencies of 20 kHz and higher). In some embodiments, the ultrasonic frequency is detected for a particular range or is detected when above or below a threshold. In some embodiments, the environmental sensor includes sound pressure sensor (e.g., that detects sound pressure when within a range of 7 dB or detects sound pressure at 120 dB or higher).

In some embodiments, the one or more environmental sensors comprise an oxygen sensor and a toxic gas sensor. In an embodiment, environmental data is received from the oxygen sensor that is below a threshold and environmental data received from the toxic gas sensor is above another threshold. In some embodiments, the one or more environmental sensors comprise an ultraviolet sensor affixed to an outer-facing surface of the wearable. In some embodiments, the one or more environmental sensors comprise one or more of an infrared sensor, an x-ray sensor, an ultrasound sensor, a radiation sensor, or one or more combinations thereof. The environmental sensors can detect whether the environmental data from these sensors is above or below a threshold. In some embodiments, the threshold is adjusted based on the size of the wearer (e.g., weight, height, body mass index, age, muscle density).

At 304, a determination is made that the sensor data is above or below a threshold. For example, one or more sensor types may each have a different threshold. In some embodiments, the biometric data from one or more of the heart rate monitor sensor, glucose sensor, ethanol perspiration sensor and may be determined to be above or below a particular threshold. Additionally or alternatively, the environmental data from one or more of the imaging sensor, location sensor, high frequency radio sensor, ultrasonic sensor, sound pressure sensor, oxygen sensor, toxic gas sensor, ultrasound sensor, radiation sensor, ultraviolet sensor, infrared sensor, an x-ray sensor, and radiation sensor may be determined to be above or below a particular threshold.

At 306, based on the biometric data or the environmental data being above or below the threshold, a signal is generated via one or more sensation devices. As such, the wearable biometrics item transmogrifies one or more human senses by using the one or more sensation devices affixed thereon. For example, a plurality of the sensation devices can generate a haptic feedback signal based on a heart rate being above or below a threshold, a glucose level being above or below a threshold, a blood oxygen level being above or below a threshold, an ethanol perspiration concentration being above a threshold level, or one or more combinations thereof. For example, the plurality of sensation devices can be affixed to a first sleeve portion of the apparel item configured for an upper torso or a first leg portion of an apparel item configured for a lower torso, wherein the haptic feedback signal is based on one or more piezoelectric elements of the sensation devices, a particular polarity, or a particular voltage or current to cause the sensation devices to provide the haptic feedback signal. In some embodiments, the one or more sensation devices are affixed to a chest region of the biometric apparel item, a back region of the biometric apparel item, a second sleeve portion of the apparel item, a second leg portion of the apparel item, or one or more combinations thereof. In some embodiments, the sensation devices are affixed to a front portion of the apparel item that is adapted to cover a front torso area.

In an embodiment, the one or more sensation devices include a piezoelectric actuator, an eccentric rotating mass motor, a linear resonance actuator, or one or more combinations thereof. Additionally or alternatively, the one or more sensation devices can also comprise a visible light source affixed to the outer-facing surface of the biometric wearable. For example, a plurality of visible light sources affixed to an outer-facing surface of the biometrics apparel item may generate visible light via the plurality of visible light sources based on receiving additional biometric data that is above a second threshold. As another example, the plurality of visible light sources can emit a purple light based on determining that an ultraviolet index detected by an ultraviolet sensor is above a threshold. In yet another example, the plurality of visible light sources can emit a red light based on determining that environmental data detected by an infrared sensor is above a threshold. In another example, the plurality of visible light sources can emit a blue light based on determining that environmental data detected by an oxygen sensor is above a threshold.

In some embodiments, the one or more sensation devices can release a scented spray in response to receiving the environmental data, from the toxic gas sensor, that is above the threshold. In some embodiments, the scented spray is released in response to determining that ammonia gas, carbon dioxide, carbon monoxide, hydrogen sulfide, methane gas, chlorine gas, formaldehyde gas, hydrogen gas, nitric oxide, nitrogen dioxide, other types of toxic or combustible gases, or one or more combinations thereof are above a threshold. For example, the scented spray may be housed in a pressure chamber, and the sensation device may also include a pressure spring and pressure piston. In some embodiments, the scented spray may comprise ammonium sulphide. In some embodiments, the one or more sensation devices can release the scented spray in response to determining that a sodium concentration determined using the sweat sensor is above a threshold or below another threshold.

Figure 4:
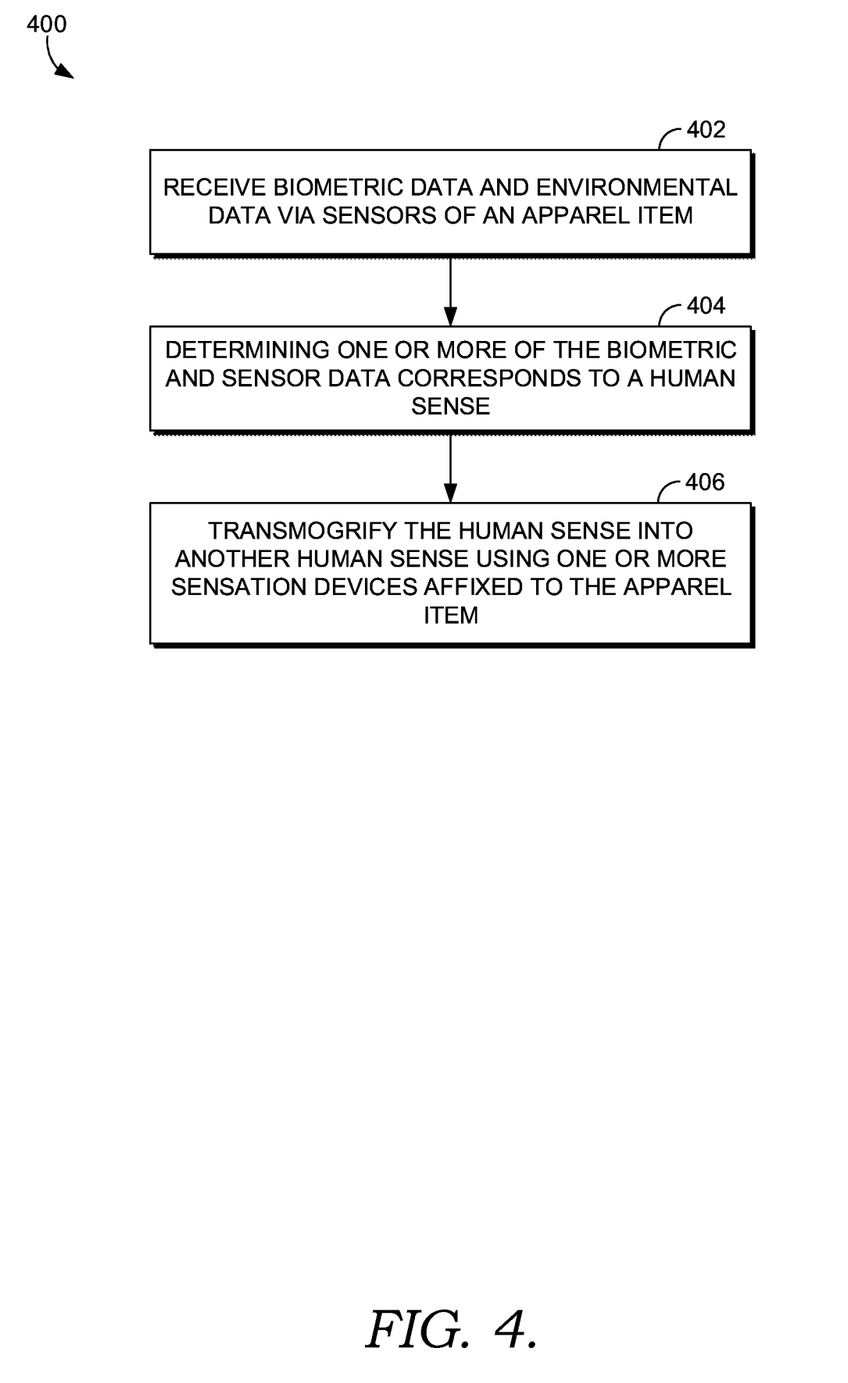
FIG. 4 depicts another flow diagram of an example method for indoor communications with biometric apparel systems and user devices, in accordance with aspects herein.

FIG. 4 depicts example method 400 for indoor communications with biometric apparel systems and user devices. At 402, sensors affixed to an apparel item receive biometric data and environmental data. Based on receiving the biometric data and the environmental data, a computer processing unit or a user device receiving the biometric and environmental data from the apparel item determine that the environmental data, the biometric data, or a combination thereof, correspond to a human sense (e.g., hearing) at 404. At 406, the apparel item transmogrifies the human sense into another human sense (e.g., touch) using the one or more sensation devices affixed to the apparel item. For example, the sensation devices can generate a haptic feedback signal (e.g., mechanical vibrations, features changes to an inner-surface of an apparel item (e.g., temperature), changes in surface tension of the inner-surface of the apparel item, electric pulses, another type of stimuli that can be perceived through non-visual, touch-based senses, or one or more combinations thereof). In some embodiments, the one or more sensation devices generate a series of tactile feedback responses.

Example Control Unit

Figure 5:
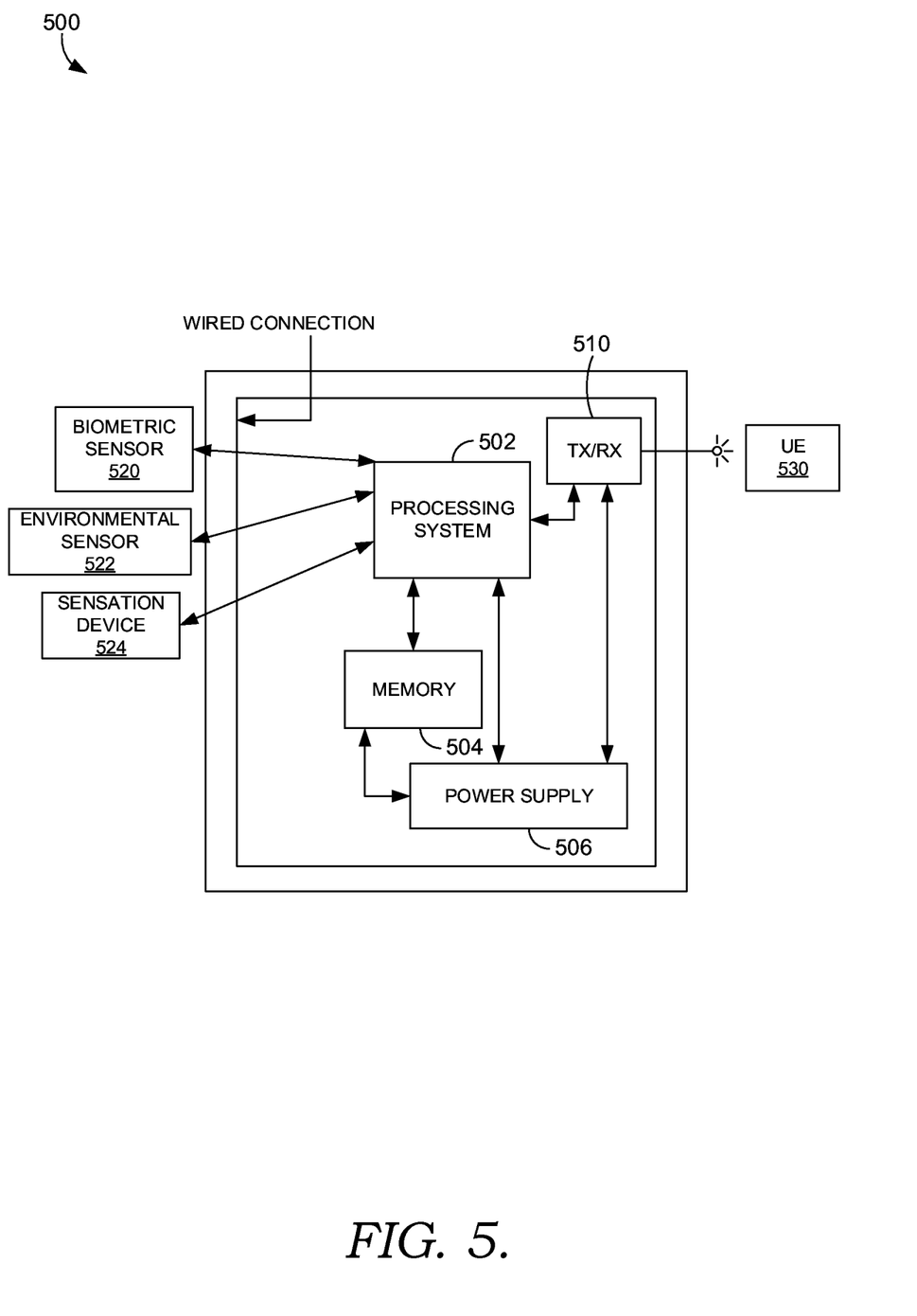
FIG. 5 depicts an example controller affixed to a biometrics apparel system that transmogrifies one or more human senses using one or more sensation devices, in accordance with aspects herein.

Having described the example embodiments discussed above of the presently disclosed technology, an example operating environment of an example control unit (e.g., control unit 122 of FIG. 1) is described below with respect to FIG. 5. Control unit environment 500 is but one example of a suitable environment and is not intended to suggest any particular limitation as to the scope of use or functionality of the technology disclosed. Neither should control unit environment 500 be interpreted as having any dependency or requirement relating to any particular component illustrated, or a particular combination of the components illustrated in FIG. 5.

Figure 6:
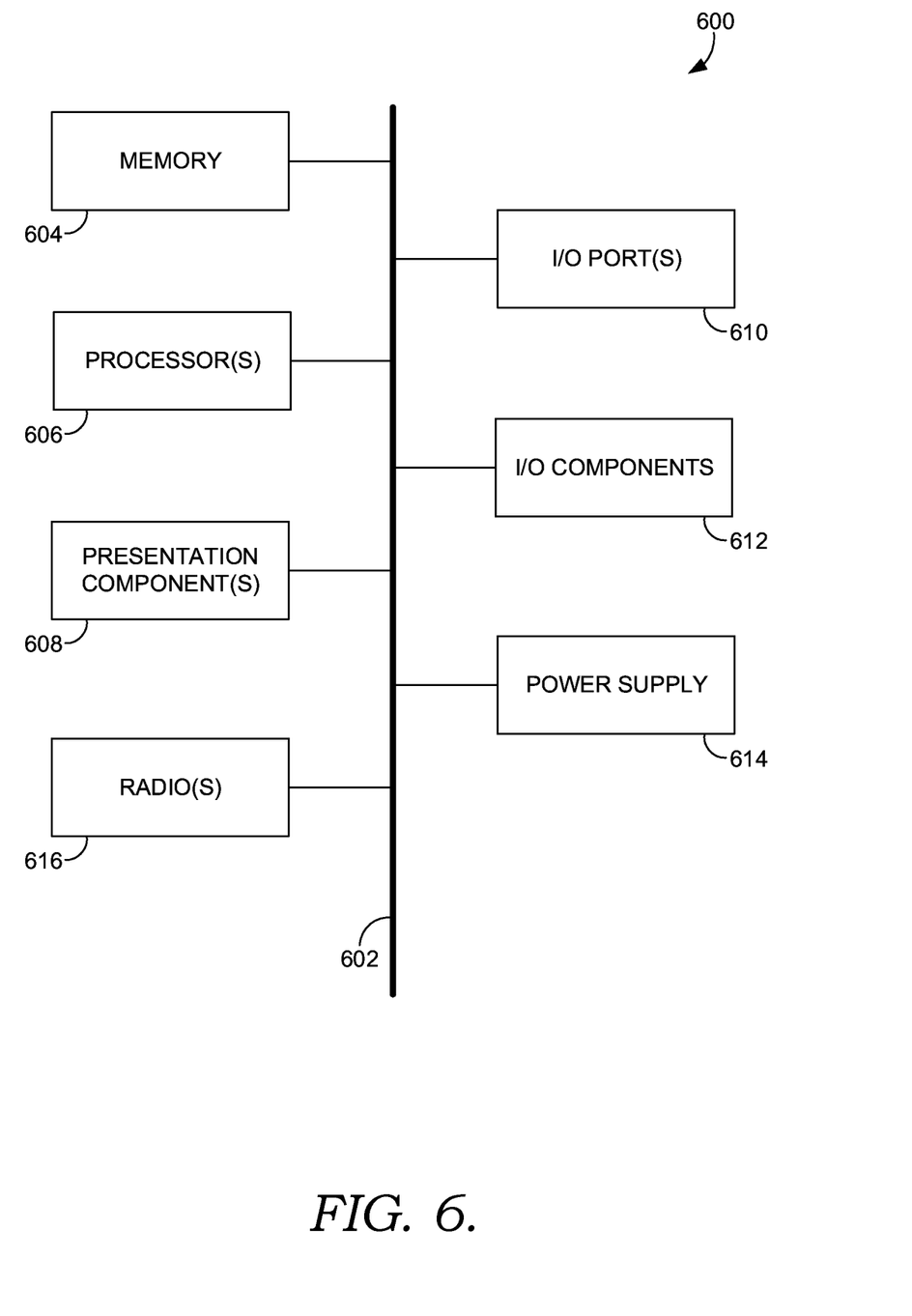
FIG. 6 depicts an example user device suitable for use in implementations of the present disclosure, in accordance with aspects herein.

Example control unit environment 500 comprises processing system 502, memory 504, power supply 506, transmitting and receiving component 510, biometric sensor 520 (e.g., biometric sensors 124A, 124B, 124C, 124D, 124E, 124F of FIG. 1), environmental sensor 522 (e.g., environmental sensors 126A, 126B of FIG. 1), sensation device 524 (e.g., sensation devices 128A, 128B, 128C, 128D, 128E, 128F of FIG. 1), and UE 530 (e.g., user device 102 of FIG. 1 or user device 600 of FIG. 6).

The processing system 502 can process data received by the biometric sensor 520, the environmental sensor 522, the sensation device 524, and the UE 530. In some embodiments, the processing system 502 may include one or more microprocessors. The memory 504 can store a program for processing and controlling the control unit environment 500. For example, the program can include a flash memory, a hard disk memory, RAM, ROM, card memory (e.g., SD card, XD memory), SRAM, EEPROM, PROM, a magnetic memory, a magnetic disc, an optical disc, other types of memory, or one or more combinations thereof. The power supply 506 may comprise a battery or another power source, for example. Transmitting and receiving component 510 can transmit and receive data from the UE 530 (as well as wearable manager 110 and wearable database 112 of FIG. 1, for example). The transmitting and receiving component 510 can also communicate with the biometric sensor 520, the environmental sensor 522, and the sensation device 524 via a wired or wireless interface, for example.

Example User Device

Having described the example embodiments discussed above of the presently disclosed technology, an example operating environment of an example user device (e.g., user device 102 of FIG. 1) is described below with respect to FIG. 6. User device 600 is but one example of a suitable computing environment and is not intended to suggest any particular limitation as to the scope of use or functionality of the technology disclosed. Neither should user device 600 be interpreted as having any dependency or requirement relating to any particular component illustrated, or a particular combination of the components illustrated in FIG. 6.

As illustrated in FIG. 6, example user device 600 includes a bus 602 that directly or indirectly couples the following devices: memory 604, one or more processors 606, one or more presentation components 608, one or more input/output (I/O) ports 610, one or more I/O components 612, a power supply 614, and one or more radios 616.

Bus 602 represents what may be one or more busses (such as an address bus, data bus, or combination thereof). Although the various blocks of FIG. 6 are shown with lines for the sake of clarity, in reality, these blocks represent logical, not necessarily actual, components. For example, one may consider a presentation component, such as a display device, to be an I/O component. Also, processors have memory. Accordingly, FIG. 6 is merely illustrative of an exemplary user device that can be used in connection with one or more embodiments of the technology disclosed herein.

User device 600 can include a variety of computer-readable media. Computer-readable media can be any available media that can be accessed by user device 600 and may include both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information, such as computer-readable instructions, data structures, program modules, or other data. Computer storage media includes, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage devices, or any other medium which can be used to store the desired information and which can be accessed by user device 600. Computer storage media does not comprise signals per se. Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared, and other wireless media. One or more combinations of any of the above should also be included within the scope of computer-readable media.

Memory 604 includes computer storage media in the form of volatile and/or nonvolatile memory. The memory 604 may be removable, non-removable, or a combination thereof. Example hardware devices of memory 604 may include solid-state memory, hard drives, optical-disc drives, other hardware, or one or more combinations thereof. As indicated above, the computer storage media of the memory 604 may include RAM, Dynamic RAM, ROM, EEPROM, flash memory or other memory technology, CD-ROM, a cache memory, DVDs or other optical disk storage, magnetic cassettes, magnetic tape, magnetic disk storage or other magnetic storage devices, a short-term memory unit, a long-term memory unit, any other medium which can be used to store the desired information and which can be accessed by user device 600, or one or more combinations thereof.

The one or more processors 606 of user device 600 can read data from various entities, such as the memory 604 or the I/O component(s) 612. The one or more processors 606 may include, for example, one or more microprocessors, one or more CPUs, a digital signal processor, one or more cores, a host processor, a controller, a chip, a microchip, one or more circuits, a logic unit, an integrated circuit (IC), an application-specific IC (ASIC), any other suitable multipurpose or specific processor or controller, or one or more combinations thereof. In addition, the one or more processors 606 can execute instructions, for example, of an operating system of the user device 600 or of one or more suitable applications.

The one or more presentation components 608 can present data indications via user device 600, another user device, or a combination thereof. Example presentation components 608 may include a display device, speaker, printing component, vibrating component, another type of presentation component, or one or more combinations thereof. In some embodiments, the one or more presentation components 608 may comprise one or more applications or services on a user device, across a plurality of user devices, or in the cloud. The one or more presentation components 608 can generate user interface features, such as graphics, buttons, sliders, menus, lists, prompts, charts, audio prompts, alerts, vibrations, pop-ups, notification-bar or status-bar items, in-app notifications, other user interface features, or one or more combinations thereof. For example, the one or more presentation components 608 can present a visualization that compares a plurality of inspections of one or more cores of a central processing unit and a visualization of each task of each of the plurality of inspections.

The one or more I/O ports 610 allow user device 600 to be logically coupled to other devices, including the one or more I/O components 612, some of which may be built in. Example I/O components 612 can include a microphone, joystick, game pad, satellite dish, scanner, printer, wireless device, and the like. The one or more I/O components 612 may, for example, provide a natural user interface (NUI) that processes air gestures, voice, or other physiological inputs generated by a user. In some instances, the inputs the user generates may be transmitted to an appropriate network element for further processing. An NUI may implement any combination of speech recognition, touch and stylus recognition, facial recognition, biometric recognition, gesture recognition both on screen and adjacent to the screen, air gestures, head and eye tracking, and touch recognition associated with the one or more presentation components 608 on the user device 600. In some embodiments, the user device 600 may be equipped with one or more imaging devices, such as one or more depth cameras, one or more stereoscopic cameras, one or more infrared cameras, one or more RGB cameras, another type of imaging device, or one or more combinations thereof, (e.g., for gesture detection and recognition). Additionally, the user device 600 may, additionally or alternatively, be equipped with accelerometers or gyroscopes that enable detection of motion. In some embodiments, the output of the accelerometers or gyroscopes may be provided to the one or more presentation components 608 of the user device 600 to render immersive augmented reality or virtual reality.

The power supply 614 of user device 600 may be implemented as one or more batteries or another power source for providing power to components of the user device 600. In embodiments, the power supply 614 can include an external power supply, such as an AC adapter or a powered docking cradle that supplements or recharges the one or more batteries. In aspects, the external power supply can override one or more batteries or another type of power source located within the user device 600.

Some embodiments of user device 600 may include one or more radios 616 (or similar wireless communication components). The one or more radios 616 can transmit, receive, or both transmit and receive signals for wireless communications. In embodiments, the user device 600 may be a wireless terminal adapted to receive communications and media over various wireless networks. User device 600 may communicate using the one or more radios 616 via one or more wireless protocols, such as code division multiple access ("CDMA"), global system for mobiles ("GSM"), time division multiple access ("TDMA"), another type of wireless protocol, or one or more combinations thereof. In embodiments, the wireless communications may include one or more short-range connections (e.g., a Wi-Fi® connection, a Bluetooth connection, a near-field communication connection), a long-range connection (e.g., CDMA, GPRS, GSM, TDMA, 602.16 protocols), or one or more combinations thereof. In some embodiments, the one or more radios 616 may facilitate communication via radio frequency signals, frames, blocks, transmission streams, packets, messages, data items, data, another type of wireless communication, or one or more combinations thereof. The one or more radios 616 may be capable of transmitting, receiving, or both transmitting and receiving wireless communications via mmWaves, FD-MIMO, massive MIMO, 3G, 4G, 5G, 6G, another type of Generation, 802.11 protocols and techniques, another type of wireless communication, or one or more combinations thereof.

Having identified various components utilized herein, it should be understood that any number of components and arrangements may be employed to achieve the desired functionality within the scope of the present disclosure. For example, the components in the embodiments depicted in the figures are shown with lines for the sake of conceptual clarity. Other arrangements of these and other components may also be implemented. For example, although some components are depicted as single components, many of the elements described herein may be implemented as discrete or distributed components or in conjunction with other components, and in any suitable combination and location. Some elements may be omitted altogether. Moreover, various functions described herein as being performed by one or more entities may be carried out by hardware, firmware, and/or software. For instance, various functions may be carried out by a processor executing instructions stored in memory. As such, other arrangements and elements (for example, machines, interfaces, functions, orders, and groupings of functions, and the like) can be used in addition to, or instead of, those shown.

Embodiments of the present disclosure have been described with the intent to be illustrative rather than restrictive. Embodiments described in the paragraphs above may be combined with one or more of the specifically described alternatives. In particular, an embodiment that is claimed may contain a reference, in the alternative, to more than one other embodiment. The embodiment that is claimed may specify a further limitation of the subject matter claimed. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims.

Many different arrangements of the various components depicted, as well as components not shown, are possible without departing from the scope of the claims below. Embodiments in this disclosure are described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims In the preceding detailed description, reference is made to the accompanying drawings which form a part hereof wherein like numerals designate like parts throughout, and in which is shown, by way of illustration, embodiments that may be practiced. It is to be understood that other embodiments may be utilized and structural or logical changes may be made without departing from the scope of the present disclosure. Therefore, the preceding detailed description is not to be taken in the limiting sense, and the scope of embodiments is defined by the appended claims and their equivalents.

The invention claimed is:

1. A biometrics apparel system comprising:
   an apparel item, the apparel item comprising at least a front portion and a back portion;
   one or more biometric sensors affixed to the apparel item for receiving biometric data;
   one or more environmental sensors affixed to the apparel item for receiving environmental data; and
   one or more sensation devices affixed to the apparel item, wherein the biometrics apparel system transmogrifies one or more human senses into a different human sense by using the one or more sensation devices and a telecommunications network, the transmogrification of the one or more human senses based on the biometric data received by the one or more biometric sensors and the environmental data received by the one or more environmental sensors.

2. The biometrics apparel system of claim 1, wherein the one or more sensation devices comprises a plurality of sensation devices that generate a haptic feedback signal.

3. The biometrics apparel system of claim 2, wherein at least one of the plurality of sensation devices is affixed to a first sleeve portion of the apparel item; wherein the one or more environmental sensors comprise an imaging sensor and a location sensor, wherein the imaging sensor is affixed to the first sleeve portion of the apparel item, and wherein the plurality of sensation devices generate the haptic feedback signal based on the biometric data received by the imaging sensor and the location sensor.

4. The biometrics apparel system of claim 3, wherein the apparel item is configured for an upper torso, wherein at least one of the plurality of sensation devices is affixed to the front portion of the apparel item that is adapted to cover a front torso area, wherein the one or more biometric sensors include a heart rate sensor, and wherein the haptic feedback signal is generated in response to receiving the biometric data, from the heart rate sensor, that is above a threshold.

5. The biometrics apparel system of claim 1, wherein the one or more environmental sensors comprise an ammonia sensor, and wherein the transmogrification of the one or more human senses is based on the environmental data, from the ammonia sensor, that is within a first threshold range.

6. The biometrics apparel system of claim 1, wherein the one or more environmental sensors comprise a sound pressure sensor, and wherein the biometrics apparel system transmogrifies the one or more human senses using the one or more sensation devices in response to:
   receiving the environmental data, from the sound pressure sensor, that is above threshold.

7. The biometrics apparel system of claim 6, wherein the one or more sensation devices release a scented spray in response to receiving the environmental data, from the sound pressure sensor, that is above the threshold.

8. A method for utilizing a biometrics apparel item, the method comprising:
   receiving, from one or more wavelength sensors affixed to the biometrics apparel item, environmental data associated with a measurement of one or more wavelengths outside of the visible light spectrum;
   determining that the environmental data received from the one or more wavelength sensors is above a threshold; and
   based on the environmental data being above the threshold, generating a color from a visible light source affixed to an outer-facing surface of the biometrics apparel item, wherein the color is associated with the environmental data.

9. The method of claim 8, wherein the biometrics apparel item has an inner-facing surface, wherein the one or more wavelength sensors comprise an ultraviolet sensor affixed to the outer-facing surface.

10. The method of claim 9, further comprising:
    determining an ultraviolent index based on the environmental data received from the ultraviolet sensor;
    determining that the ultraviolent index is above the threshold; and
    emitting a purple light from the visible light source.

11. The method of claim 8, wherein the one or more wavelength sensors comprise an infrared sensor, and generating a red light from the visible light source based on the environmental data detected by the infrared sensor being above the threshold.

12. The method of claim 8, wherein the method further comprises:
    receiving biometric data from one or more biometric sensors affixed to the biometrics apparel item, wherein the one or more biometric sensors include a sweat sensor and the biometric data includes sweat data;
    determining a sodium concentration from the sweat data;
    determining that the sodium concentration is above a second threshold or below a third threshold; and
    generating a signal via one or more sensation devices affixed to the biometrics apparel item based on determining that the sodium concentration is above the second threshold or below the third threshold.

13. The method of claim 12, further comprising transmitting a notification to a user device associated with the biometrics apparel item based on determining that the sodium concentration is above the second threshold or below the third threshold.

14. The method of claim 12, wherein the biometrics apparel item comprises a radiation sensor, and wherein the method further comprises generating the signal via the one or more sensation devices based on determining that data received from the radiation sensor is above a threshold.

15. The method of claim 12, wherein the biometrics apparel item comprises a gas sensor, and wherein the method further comprises generating the signal via the one or more sensation devices based on determining that combustible or toxic gas environmental data received by the gas sensor is above a threshold.

16. A system for operating a biometrics apparel item, the system comprising:
one or more processors; and
one or more computer storage memory having computer-executable instructions stored thereon that, when executed by the one or more processors, cause the system to perform operations comprising:
receive, from one or more biometric sensors affixed to the biometrics apparel item, biometric data;
determine that the biometric data received from the one or more biometric sensors is above a threshold; and
based on the biometric data being above the threshold, cause one or more sensation devices of the biometrics apparel item to release a scented spray.

17. The system of claim 16, wherein the biometrics apparel item comprises a plurality of visible light sources affixed to an outer-facing surface of the biometrics apparel item, and wherein the operations further cause the biometrics apparel item to generate visible light via the plurality of visible light sources based on receiving additional biometric data that is above a second threshold.

18. The system of claim 16, wherein the one or more biometric sensors comprises an ethanol perspiration sensor.

19. The biometrics apparel system of claim 1, wherein the one or more environmental sensors comprise a formaldehyde sensor, and wherein the transmogrification of the one or more human senses is based on the environmental data, from the formaldehyde sensor, being within a first threshold range.

20. The method of claim 8, further comprising:
receiving, from one or more oxygen sensors affixed to the biometrics apparel item, oxygen data;
determining that the oxygen data received from the one or more oxygen sensors is below a second threshold; and
based on the oxygen data being below the second threshold, generating a blue light from a second visible light source affixed to the biometrics apparel item.

* * * * *